US005700670A

United States Patent [19]
Yamagishi et al.

[11] Patent Number: 5,700,670
[45] Date of Patent: Dec. 23, 1997

[54] METHOD FOR PRODUCING OPTICALLY ACTIVE ESTER OF γ-SUBSTITUTED-β-HYDROXYBUTYRIC ACID

[75] Inventors: Masahiro Yamagishi; Makoto Ueda; Yukie Takai; Mari Yasuda; Takashi Mikawa, all of Yokohama, Japan

[73] Assignee: Mitsubishi Chemical Corporation, Tokyo, Japan

[21] Appl. No.: 630,623

[22] Filed: Apr. 10, 1996

[30] Foreign Application Priority Data

Apr. 13, 1995 [JP] Japan .................................. 7-087934
Apr. 8, 1996 [JP] Japan .................................. 8-085517

[51] Int. Cl.⁶ .............................. C12P 13/00; C12P 7/62
[52] U.S. Cl. ............................ 435/128; 435/135; 435/911
[58] Field of Search ........................ 435/135, 128, 435/911

[56] References Cited

FOREIGN PATENT DOCUMENTS

| | | |
|---|---|---|
| 0 352 092 | 1/1990 | European Pat. Off. . |
| 0 606 899 | 7/1994 | European Pat. Off. . |
| 62-126997 | 6/1987 | Japan . |
| 63-309195 | 12/1988 | Japan . |
| 1-117792 | 5/1989 | Japan . |
| 4-7195 | 2/1992 | Japan . |
| 6-38776 | 2/1994 | Japan . |
| 6-209782 | 8/1994 | Japan . |

OTHER PUBLICATIONS

Chemical Abstracts, 104(25):223632z (1986).

*Primary Examiner*—Herbert J. Lilling
*Attorney, Agent, or Firm*—Wenderoth, Lind & Ponack

[57] ABSTRACT

Microbial cells and/or a preparation therefrom of a microorganism is allowed to act on an ester of γ-substituted-acetoacetic acid, and a carbonyl group at its β-position is stereospecifically reduced, wherein the microorganism is selected from the group consisting of those belonging to the genera Yarrowia, Filobasidium, Metschnikowia, Galactomyces, Ambrosiozyma, Trichosporonoides, Aureobasidium, Phaeococcomyces, Rosulomyces, Dothichiza, Emericellopsis, Calonectria, Colletotrichum, and Ceratocystis, preferably, the microorganism is microorganism belonging to the genus Aureobasidium. Thus an optically active ester of γ-substituted-β-hydroxybutyric acid having a high optical purity is produced in a short period of time at a high accumulated concentration and a high yield.

7 Claims, No Drawings

METHOD FOR PRODUCING OPTICALLY ACTIVE ESTER OF γ-SUBSTITUTED-β-HYDROXYBUTYRIC ACID

FIELD OF THE INVENTION

The present invention relates to a method for producing an optically active ester of γ-substituted-β-hydroxybutyric acid, and a novel microorganism. In particular, the present invention relates to a method for efficiently producing an optically active ester of γ-substituted-β-hydroxybutyric acid having a high optical purity, and a novel microorganism belonging to the genus Aureobasidium.

BACKGROUND OF THE INVENTION

The optically active ester of γ-substituted-β-hydroxybutyric acid is useful as a material for synthesizing optically active compounds or intermediates for synthesizing such compounds which are utilized for various pharmaceuticals, agricultural chemicals and so on. For example, this ester can be converted into a side chain portion of an optically active hydroxy acid derivative which is common to various HMG-CoA reductase inhibitors (therapeutic agents for hyperlipemia) such as compactin and pravastatin. In relation to the production of the optically active ester of γ-substituted-β-hydroxybutyric acid, it has been hitherto investigated to utilize the microbial ability to perform asymmetric reduction. There are numerous reports on examples of such type of production.

Among such type of methods for producing the optically active ester of γ-substituted-β-hydroxybutyric acid, especially the following methods are known as methods for producing an optically active ester of γ-halogenated-β-hydroxybutyric acid. Namely, for example, there are known a method to use microbial cells of yeasts or the like belonging to the genera Candida, Debaryomyces, Saccharomyces, Pichia, Hansenula, etc. (Japanese Patent Publication No. 4-7195); a method to use a culture broth or separated microbial cells of fungi belonging to the genera Stemphylium, Alternaria, Corynespora, Preussia, etc. (Japanese Patent Laid-open No. 6-38776); a method to use microbial cells of bacteria belonging to the genera Brevibacterium, Escherichia, Lactobacillus, etc. or yeasts or the like belonging to the genera Kluyveromyces, Saccharomycopsis, Stephanoascus, etc. (Japanese Patent Laid-open No. 6-209782); and a method to perform a reaction in a two-phase system of water and organic solvent by using an enzyme obtained from yeasts, fungi or the like belonging to the genera Rhodotorula, Fusarium, Paecilomyces, Verticillium, etc. (Japanese Patent Laid-open No. 63-309195).

However, any of the production methods described above has had the following problems. Namely, for example, species of microorganisms being used (in the production) are limited, the reaction velocity is small, the reaction is time-consuming, and the concentration of accumulated product cannot be increased. Additionally, the production methods described above merely provide a product having a low optical purity.

SUMMARY OF THE INVENTION

Because of such circumstances, it has been desired to establish an excellently economical method which makes it possible to produce an optically active ester of γ-substituted-β-hydroxybutyric acid having a high optical purity, at a high accumulated concentration and a high yield.

The present invention has been made considering the viewpoint as described above, an object of which is to provide a method for producing an optically active ester of γ-substituted-β-hydroxybutyric acid having a high optical purity, in a short period of time at a high accumulated concentration and a high yield.

As a result of diligent investigations by the present inventors in order to achieve the object described above by developing an efficient production method for an optically active ester of γ-substituted-β-hydroxybutyric acid, it has been found that the optically active ester of γ-substituted-β-hydroxybutyric acid having a high optical purity can be obtained in a short period of time at a high accumulated concentration and a high yield by allowing microbial cells and/or a preparation therefrom of a specified microorganism to act on an ester of γ-substituted-acetoacetic acid, the microorganism being not described in any of the documents described above. Moreover, the present inventors have succeeded in obtaining a novel microorganism belonging to the genus Aureobasidium through a process of screening for microorganisms useful for the production method described above. Thus the present invention has been completed.

Namely, the present invention lies in a method for producing an optically active ester of γ-substituted-β-hydroxybutyric acid, comprising the steps of:

allowing microbial cells and/or a preparation therefrom of a microorganism to act on an ester of γ-substituted-acetoacetic acid represented by a general formula (1);

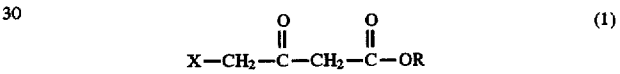

wherein X represents a halogen atom, a cyano group, or a protected or unprotected aminomethyl group, and R represents a lower alkyl group in the general formula (1);

wherein the microorganism has an ability to stereospecifically reduce a carbonyl group at a β-position of the ester of γ-substituted-acetoacetic acid represented by the general formula (1), and the microorganism is selected from the group consisting of those belonging to the genera Yarrowia, Filobasidium, Metschnikowia, Galactomyces, Ambrosiozyma, Trichosporonoides, Aureobasidium, Phaeococcomyces, Rosulomyces, Dothichiza, Emericellopsis, Calonectria, Colletotrichum, and Ceratocystis; and stereospecifically reducing the carbonyl group at the β-position to produce the optically active ester of γ-substituted-β-hydroxybutyric acid represented by a general formula (2);

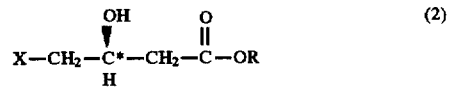

wherein X and R in the general formula (2) are synonymous with X and R in the general formula (1).

The present invention further provides a novel microorganism of *Aureobasidium pullulans* with its hyphal cell wall which does not thicken.

According to the production method of the present invention described above, the optically active ester of γ-substituted-β-hydroxybutyric acid having a high optical purity can be produced in a short period of time at a high yield and a high accumulated concentration, which is extremely advantageous from the viewpoint of industrial production.

3

The *Aureobasidium pullulans* of the present invention is a novel microorganism having a feature that its hyphal cell wall does not thicken. This feature has not been observed for conventionally known species of *Aureobasidium pullulans*.

DETAILED DESCRIPTION OF THE INVENTION

The present invention will be explained in detail below.

(1) Optically active ester of γ-substituted-β-hydroxybutyric acid obtained by the production method of the present invention In the production method of the present invention, the "ester of γ-substituted-acetoacetic acid" represented by the general formula (1) is used as a material on which the microbial cells and/or the preparation therefrom of the specified microorganism is allowed to act to produce the "optically active ester of γ-substituted-β-hydroxybutyric acid" represented by the general formula (2). In both of the general formulas (1) and (2) described above, X represents a halogen atom, a cyano group, or a protected or unprotected aminomethyl group. As referred to herein, the halogen atom includes, for example, chlorine atom, bromine atom, and iodine atom. The protected or unprotected aminomethyl group includes, for example, unprotected aminomethyl group as well as protected aminomethyl groups protected by a protective group such as benzyloxycarbonyl group and t-butoxycarbonyl group. Among the preferred atoms or groups described above, X is preferably a halogen atom, aminomethyl group, or benzyloxycarbonylaminomethyl group in the present invention.

In the general formulas (1) and (2) described above, R represents a lower alkyl group. As referred to herein, the lower alkyl group may preferably include, for example, lower alkyl groups having a number of carbons of 1 to 4, such as methyl group, ethyl group, n-propyl group, isopropyl group, n-butyl group, isobutyl group, and t-butyl group.

The optically active ester of γ-substituted-β-hydroxybutyric acid represented by the general formula (2) is a (3S)-hydroxy compound when X is a halogen atom, or it is a (3R)-hydroxy compound when X is a cyano group or a protected or unprotected aminomethyl group.

In the production method of the present invention, X is preferably a chlorine atom, and R is an ethyl group in the general formulas (1) and (2) described above. Namely, according to the production method of the present invention, ethyl (S)-γ-chloro-β-hydroxybutyrate can be produced more efficiently (at a higher accumulated concentration and a higher yield) when ethyl γ-chloro-acetoacetate is used as a raw material.

(2) Microbial cells and/or preparation therefrom of microorganism used in production method of the present invention, and novel microorganism of the present invention In the production method of the present invention, the microbial cells and/or the preparation therefrom of the microorganism is allowed to act on the ester of γ-substituted-acetoacetic acid represented by the general formula (1) as described above and stereospecifically reduce its carbonyl group at the β-position, the microorganism being selected from the group consisting of those belonging to the genera Yarrowia, Filobasidium, Metschnikowia, Galactomyces, Ambrosiozyma, Trichosporonoides, Aureobasidium, Phaeococcomyces, Rosulomyces, Dothichiza, Emericellopsis, Calonectria, Colletotrichum, and Ceratocystis. Thus the optically active ester of γ-substituted-β-hydroxybutyric acid represented by the general formula (2) is produced.

The microorganisms used in the production method of the present invention is not specifically limited provided that is

4 has the ability to act on the carbonyl group at the β-position of the ester of γ-substituted-acetoacetic acid and stereospecifically reduce (asymmetrically reduce) it. Those preferred may include, for example, *Yarrowia lipolytica*, *Filobasidium capsuligenum*, *Metschnikowia lunata*, *Metschnikowia bicuspidata*, *Galactomyces reesii*, *Ambrosiozyma platypodis*, *Trichosporonoides spathulata*, *Aureobasidium pullulans*, *Phaeococcomyces nigricans*, *Rosulomyces arthrosporioides*, *Dothichiza ferruginea*, *Emericellopsis synnematicola*, *Calonectria kyotoensis*, *Colletotrichum pisi*, and *Ceratocystis bacillospora*, judging from the ability to act on the carbonyl group at the β-position of the ester of γ-substituted-acetoacetic acid and stereospecifically reduce it. Among these microorganisms, more preferred microorganisms may be represented by microorganisms belonging to the genus Aureobasidium and further preferred microorganisms may be represented by *Aureobasidium pullulans*, judging from the reducing ability as described above.

Specified microbial strains of the microorganisms described above include, for example, the following microbial strains:

*Yarrowia lipolytica* IFO 1209;
*Yarrowia lipolytica* ATCC 8661;
*Filobasidium capsuligenum* IFO 1119;
*Metschnikowia lunata* IFO 1605;
*Metschnikowia bicuspidata* IFO 1408;
*Galactomyces reesii* IFO 1112;
*Ambrosiozyma platypodis* IFO 1471;
*Trichosporonoides spathulata* CBS 241.79;
*Aureobasidium pullulans* CBS 105.22;
*Aureobasidium pullulans* CBS 702.76;
*Aureobasidium pullulans* ATCC 34621;
*Aureobasidium pullulans* MCI 3251;
*Aureobasidium pullulans* MCI 3252;
*Phaeococcomyces nigricans* CBS 652.76;
*Rosulomyces arthrosporioides* CBS 506.76;
*Dothichiza ferruginea* ATCC 11918;
*Emericellopsis synnematicola* IFO 9042;
*Calonectria kyotoensis* ATCC 18834;
*Colletotrichum pisi* ATCC 12520; and
*Ceratocystis bacillospora* ATCC 26400.

The microorganisms described above may be any type of strains including, for example, wild strains, mutant strains, and recombinant strains derived by genetic techniques such as cell fusion and genetic recombination methods.

As for the microbial strains described above, all of the microbial strains except for *Aureobasidium pullulans* MCI 3251 and Aureobasidium pullulans MCI 3252 are known microbial strains. They are readily available from Institute for Fermentation, Osaka (IFO), The American Type Culture Collection (ATCC), and Centraalbureau voor Schimmelcultures (CBS), respectively.

*Aureobasidium pullulans* MCI 3251 and *Aureobasidium pullulans* MCI 3252 described above are microbial strains newly discovered from the nature by the present inventors, and they have been deposited in National Institute of Bioscience and Human Technology of Agency of Industrial Science and Technology of Ministry of International Trade and Industry (1–3, Higashi 1-chome, Tsukuba-shi, Ibaraki-ken 305, Japan) on Feb. 27, 1996 under microorganism deposition numbers of FERM BP-5425 and FERM BP-5426, respectively. Microbiological properties of these microbial strains are shown below.

(A) *Aureobasidium pullulans* MCI 3251
(1) Morphological properties
This strain grows vigorously upon cultivation at 24° C. on a potato dextrose agar (PDA) medium.

Colonies are smooth, having a color which is initially light brown, but gradually changes to yellowish brown to black at peripheral portions.

Young hyphae are 3.8 to 6.3 μm in width, branched and colorless, and they have septa. As a culture becomes old, the hyphae undergo change in color to brown, and they develop to have thick walls, followed by fragmentation into arthro-type chlamydospores.

Chlamydospore has a size of 7.8 to 9.4×10 to 14 μm, and it is one- or two-celled. Its shape is elliptical and smooth, having a brown color.

Conidiogenous cells are undifferentiated, which are composed of spinulose projections laterally developed from hyphae. Conidia are synchronously formed by budding from the spinulose projections. Secondary conidia are often formed from primary conidia through a process of yeast-like budding. The conidia adhere in slimy heads, and are abundant in variation. The conidia have a size of 3.0 to 5×5 to 11.6 μm, and an elliptical or elongated elliptical shape, and they are colorless and smooth. Each of them is one-celled.

(2) Physiological properties

Growth ranges are as follows.

pH: 3 to 11 (as measured by cultivation for 7 days in an LCA liquid medium);

temperature: 4° to 35° C. (as measured by cultivation for 12 days on a PDA agar medium);

optimum growth temperature: 20° to 30° C.

(3) Taxonomical remarks

The genus Aureobasidium is characterized in that (1) budding type conidia are synchronously formed from undifferentiated hyphae, and (2) the hyphae change in color to brown as the culture becomes old to cause arthro-type fragmentation followed by formation of arthro-type chlamydospores. The genus Hormonema is closely related to the genus Aureobasidium. However, this genus is distinguished from the genus Aureobasidium based on the fact that conidia are formed basipetally, and brown hyphae are not fragmented.

The microbial strain MCI 3251 referred to herein is characterized in that (1) budding type conidia are formed, and (2) old hyphae become brown, and they are fragmented into arthro-type spores. Accordingly, it has been revealed that the microbial strain MCI 3251 belongs to the genus Aureobasidium. Further, the microbial strain MCI 3251 has been searched for at a level of species with reference to pages 141 to 223 in a monograph written by E. J. Hermanides-Nijhof in 1977 "Aureobasidium and allied Genera". As a result, the microbial strain MCI 3251 has been identified as *Aureobasidium pullulans* because this strain has the following features, and these features are well coincident with the nature of *Aureobasidium pullulans*. Firstly, its conidia have a size of not more than 22 μm in length, and the conidia are not curved. Secondly, no sporodochium is formed in a medium. Finally, in an old culture, its hyphae become brown, and its cell walls become remarkably thick.

(B) Aureobasidium pullulans MCI 3252

(1) Morphological properties

This strain Grows vigorously upon cultivation at 24° C. on a potato dextrose agar (PDA) medium.

Colonies spread radially, and they are smooth, initially having a pale flesh color to a pale yellow color. As a culture becomes old, aerial mycelia having a white color to a brown color develop at peripheral portions.

Young hyphae are 2.8 to 3.4 μm in width, branched and colorless, and they have septa. As a culture becomes old, pale brown hyphae are locally generated. Old hyphae are 3.1 to 7.8 μm in width, and branched, and they have septa. Cell walls are thin, and brown-colored hyphae extremely scarcely cause arthro-type fragmentation.

Conidiogenous cells are undifferentiated, which are composed of spinulose projections laterally developed from hyphae. Conidia are synchronously formed by budding from forward ends of the spinulose projections. Secondary conidia are formed from primary conidia through a process of yeast-like budding. The conidia adhere in slimy heads. The conidia have a size of 2.2 to 3.8×5.3 to 9.1 μm, and a slender elliptical or oval shape, and they are colorless and smooth. Each of them is one-celled.

(2) Physiological properties

Growth ranges are as follows.

pH: 3 to 11 (as measured by cultivation for 7 days in an LCA liquid medium);

temperature: 4° to 35° C. (as measured by cultivation for 12 days on a PDA agar medium);

optimum growth temperature: 20° to 30° C.

(3) Taxonomical remarks

The microbial strain MCI 3252 referred to herein is characterized in that (1) budding type conidia are synchronously formed, and (2) as a culture becomes old, hyphae become brown, and they are sometimes fragmented in a form of the arthro-type. Accordingly, it has been revealed that the microbial strain MCI 3252 belongs to the genus Aureobasidium. The microbial strain MCI 3252 has been searched for at a level of species with reference to identification keys for species of the genus Aureobasidium described on pages 141 to 223 in a monograph written by E. J. Hermanides-Nijhof in 1977 "Aureobasidium and allied Genera".

As a result, the microbial strain MCI 3252 has the following features, and these features are coincident with the nature of *Aureobasidium pullulans*. Firstly, its conidia have a length of not more than 22 μm, and the conidia are not curved. Secondly, no sporodochium is formed in a medium. Finally, its conidia have a size of 2.2 to 3.8×5.3 to 9.1 μm. However, in relation to the feature of the cell wall of hyphae, this microbial strain is different from *Aureobasidium pullulans* in that its cell wall is thin throughout all its life cycle, and that no wall thickening is observed, which would be observed in a representative microbial strain of *Aureobasidium pullulans*. It is considered that the difference in degree of hyphal cell wall thickening is due to mutation within the species. The size and the morphological form of conidia, which are characters for identifying species, fall within the range (3.7 to 7×7.5 to 16 μm) as described for *Aureobasidium pullulans* in the monograph by E. J. Hermanides-Nijhof described above. Accordingly, this microbial strain has been identified as *Aureobasidium pullulans*.

The strain of *Aureobasidium pullulans* MCI 3252 is a novel strain of *Aureobasidium pullulans* which is different from hitherto known strains of *Aureobasidium pullulans* in that the hyphal cell wall does not thicken throughout all its life cycle as described above. Such a strain of *Aureobasidium pullulans*, which has the property that the hyphal cell wall does not thicken, can be specifically obtained in accordance with the following method.

Withered and dead plants, collected from various places in Japan without specifically limiting the type of place for collection, are directly inoculated (direct inoculation method) on a medium such as a potato dextrose agar medium on which ordinary fungi can grow, to perform cultivation at 27° C. for 3 to 7 days. Colonies appeared on the medium are inspected with a microscope. Thus colonies, considered as colonies of microorganisms belonging to the genus Aureobasidium, are selected. Microbiological properties are investigated in the same manner as described above for each of microbial strains obtained from the selected colonies. Microbial strains, identified as microorganisms belonging to the genus Aureobasidium, are identified for their species in accordance with identification keys for species of the genus Aureobasidium described on pages 141 to 223 in a monograph written by E. J. Hermanides-Nijhof in 1977 "Aureobasidium and allied Genera". In this procedure, it is possible to select a microbial strain in which the size and the morphological form of conidia as the identification characters for species are coincident with the nature of *Aureobasidium pullulans* according to the identification keys described above, but its hyphal cell wall does not thicken throughout all its life cycle. A strain of *Aureobasidium pullulans* thus obtained is the novel strain of *Aureobasidium pullulans* of the present invention.

In the production method of the present invention, one or more species of the microorganisms, which have the ability to act on the carbonyl group at the β-position of the ester of γ-substituted-acetoacetic acid described above and stereospecifically reduce (asymmetrically reduce) it, are used in the form of the microbial cells and/or the preparation therefrom. Specifically, it is possible to use the microbial cells as they are, obtained by cultivating the microorganisms described above, or it is possible to use the preparation prepared, from the microbial cells obtained by cultivation, by means of an acetone treatment or a treatment of lyophilization, or prepared by disrupting the microbial cells mechanically or enzymatically. Alternatively, it is also possible to use an enzyme fraction extracted as a crude preparation or a purified preparation which has the ability to act on the carbonyl group at the β-position of the ester of γ-substituted-acetoacetic acid represented by the general formula (1) and stereospecifically reduce (asymmetrically reduce) and convert it into the optically active ester of γ-substituted-β-hydroxybutyric acid represented by the general formula (2). Further, it is also possible to use an immobilized preparation of the microbial cells, the preparation, and the enzyme fraction obtained as described above on a carrier such as polyacrylamide gel and carageenan gel. Thus in this specification, the term "microbial cells and/or a preparation therefrom" is used as a concept which includes all of the microbial cells, the preparation, the enzyme fraction, and the immobilized preparation of them as described above.

(3) Method for producing optically active ester of γ-substituted-β-hydroxybutyric acid of the present invention Next, the method for producing the optically active ester of γ-substituted-β-hydroxybutyric acid of the present invention will be specifically explained.

In the production method of the present invention, the "ester of γ-substituted-acetoacetic acid" represented by the general formula (1) is used as a material on which the microbial cells and/or the preparation therefrom of the microorganism as specified above are allowed to act to produce the "optically active ester of γ-substituted-β-hydroxybutyric acid" represented by the general formula (2).

In the production method of the present invention, the microorganism is usually used after cultivation. The cultivation may be performed in accordance with an ordinary method. The cultivation may be performed by using a medium containing an appropriate combination of a carbon source such as glucose, sucrose, glycerol, and citric acid; an inorganic nitrogen source such as ammonium sulfate and sodium nitrate; an organic nitrogen source such as yeast extract, peptone, urea, meat extract, and corn steep liquor; inorganic salts such as salts of magnesium and potassium; phosphate and so on. In addition to these components, it is also possible to add substances for enhancing the reactivity, such as inorganic salts, trace metals, amino acids, and vitamins. The cultivation is preferably performed at a temperature of 20° to 45° C. within a range of period of 1 to 10 days while adjusting pH of the medium within a range of 4 to 10 until the activity is maximized.

In the present invention, the microbial cells and/or the preparation therefrom of the microorganism thus obtained by the cultivation are allowed to contact with the ester of γ-substituted-acetoacetic acid represented by the general formula (1) in an aqueous medium to perform the reaction so that the optically active ester of γ-substituted-β-hydroxybutyric acid represented by the general formula (2) is obtained as a reaction product. The aqueous medium used herein includes, for example, water, buffer, and culture broth. However, the aqueous medium may contain an appropriate amount of a water-soluble organic solvent or an oil-soluble organic solvent. Upon the reaction, the yield is distinctly improved by adding, to the reaction solution, a carbon source such as glucose, sucrose, fructose, ethanol, and methanol as an energy source.

The ester of γ-substituted-acetoacetic acid is added to the reaction solution in such an amount that the concentration of the ester in the reaction solution is about 0.01 to 50 w/v %. The added ester of γ-substituted-acetoacetic acid may be not necessarily dissolved completely in the aqueous medium in the reaction solution. When the reaction suffers substrate inhibition, the accumulated amount of the product can be further increased by continuously or intermittently adding the ester of γ-substituted-acetoacetic acid in an amount corresponding to a consumed amount, while the ester of γ-substituted-acetoacetic acid is consumed as the reaction proceeds. The amount of the microbial cells and/or the preparation therefrom of the microorganism to be added to the reaction solution is selected as follows. Namely, when the microbial cells are added, they are added to the reaction solution so that the concentration of the microbial cells is about 0.01 to 20 w/v %. Alternatively, when the preparation such as enzyme is used, the specific activity of the enzyme is determined to add it so that the concentration of the enzyme after the addition corresponds to the concentration of the microbial cells described above. Preferred reaction conditions in this reaction are as follows. Namely, the reaction temperature is in a range from a freezing point to 70° C., preferably 10° to 50° C., pH is 3 to 11, preferably 5 to 9, and the reaction time is about 1 to 100 hours.

As a result of the reaction described above, the optically active ester of γ-substituted-β-hydroxybutyric acid is obtained as the reaction product. The optically active ester of γ-substituted-β-hydroxybutyric acid as the objective product is isolated from the reaction mixture by means of certain methods including, for example, a method comprising the steps of removing the microbial cells and/or the preparation therefrom by centrifugation, subsequently extracting the optically active ester of γ-substituted-γ-hydroxybutyric acid from the reaction mixture with an organic solvent such as chloroform and ethyl acetate, and isolating the optically active ester by utilizing known methods such as distillation and column chromatography.

According to the production method of the present invention, the optically active ester of γ-substituted-β-hydroxybutyric acid having a high optical purity can be produced in a short period of time at a high yield and a high accumulated concentration, since the microorganism used has the ability to act on the carbonyl group at the β-position of the ester of γ-substituted-acetoacetic acid and stereospecifically reduce (asymmetrically reduce) it.

reaction product after conversion into an amount per culture broth (unit: g/L/broth).

DESCRIPTION OF THE PREFERRED EMBODIMENTS

Examples of the present invention will be explained below.

TABLE 1

| Microorganism | Yield in reaction [%] | Produced amount [g/L/broth] | Optical purity [% e.e.] | Absolute configuration |
|---|---|---|---|---|
| *Yarrowia lipotytica* IFO 1209 | 90 | 13.6 | 97 | S |
| *Yarrowia lipolytica* ATCC 8661 | 88 | 13.3 | 98 | S |
| *Filobasidium capsuligenum* IFO 1119 | 86 | 13.0 | 94 | S |
| *Metschnikowia lunata* IFO 1605 | 92 | 13.9 | 82 | S |
| *Metschnikowia bicuspidata* IFO 1408 | 89 | 13.5 | 92 | S |
| *Galactomyces reesii* IFO 1112 | 86 | 13.0 | 90 | S |
| *Ambrosiozyma platypodis* IFO 1471 | 90 | 13.6 | 84 | S |
| *Trichosporonoides spathulata* CBS 241.79 | 91 | 13.8 | 90 | S |
| *Aureobasidium pullulans* CBS 105.22 | 95 | 14.4 | 98 | S |
| *Aureobasidium pullulans* CBS 702.76 | 94 | 14.2 | 98 | S |
| *Aureobasidium pullulans* ATCC 34621 | 98 | 14.9 | 99 | s |
| *Phaeococcomyces nigricans* CBS 652.76 | 89 | 13.5 | 82 | S |
| *Rosulomyces arthrosporioides* CBS 506.76 | 98 | 14.9 | 99 | S |
| *Dothichiza ferruinea* ATCC 11918 | 89 | 13.5 | 95 | S |
| *Emericellopsis synnematicola* IFO 9042 | 86 | 13.1 | 84 | S |
| *Calonectria kyotoensis* ATCC 18834 | 90 | 13.7 | 82 | S |
| *Colletotrichum pisi* ATCC 12520 | 95 | 14.4 | 94 | S |
| *Ceratocystis bacillospora* ATCC 26400 | 93 | 14.1 | 94 | S |

Example 1

Microbial cells of various species of microorganisms shown in Table 1 were respectively inoculated to a medium (each 10 ml) containing glucose (4.0 w/v %), yeast extract (2.0 w/v %), malt extract (1.0 w/v %), and polypeptone (1.0 w/v %) at pH adjusted to 6.0, and they were cultivated aerobically at 27° C. for 1 to 2 days with shaking. After completion of the cultivation, microbial cells were collected by centrifugation, and washed with phosphate buffer (0.1M, pH 6.5). After that, the respective microbial cells were transferred to a test tube (φ21 mm), and suspended in the same buffer (5.0 ml) containing glucose (5.0 w/v %) so that the microbial cell concentration was two times that in the culture broth. An aliquot (150 mg) of ethyl γ-chloro-acetoacetate was added to each of the microbial cell suspensions to perform a reaction with shaking at 30° C. for 4 hours.

After completion of the reaction, the microbial cells were removed from each of the reaction solutions by centrifugation. The reaction supernatant was diluted with methanol to perform reverse phase HPLC analysis [Cosmosil 5C18, eluent: 20% acetonitrile aqueous solution, flow rate: 0.5 ml/minute, UV: 220 nm]. The amount of produced ethyl (S)-γ-chloro-β-hydroxybutyrate produced by the reaction described above was measured to determine the yield in reaction. On the other hand, an aliquot (10 ml) of ethyl acetate was added to each of the reaction supernatants to perform extraction followed by concentration. After that, an obtained sample was dissolved in hexane to measure the optical purity and determine the absolute configuration by means of optical resolution HPLC analysis [column: Daicel CHIRALPAK AS, eluent: hexane/isopropanol/ethanol/cyclohexanol=80/2/1/0.2, flow rate: 0.7 ml/minute, detection UV: 220 nm]. Obtained results are shown in Table 1. The produced amount in Table 1 indicates an amount of the

Example 2

Methyl (S)-γ-chloro-β-hydroxybutyrate was produced by using *Rosulomyces arthrosporioides* CBS 506.76 as the microbial cells and methyl γ-chloro-acetoacetate as the reaction substrate in accordance with the same procedure as that in Example 1. The yield in reaction and the optical purity were measured for methyl (S)-γ-chloro-β-hydroxybutyrate obtained by this reaction, in accordance with the same method as that in Example 1 described above. As a result, the yield in reaction was 98%, and the optical purity was 96% e.e.

Example 3

Ethyl (S)-γ-bromo-β-hydroxybutyrate was produced by using *Rosulomyces arthrosporioides* CBS 506.76 as the microbial cells and ethyl γ-bromo-acetoacetate as the reaction substrate in accordance with the same procedure as that in Example 1. The yield in reaction and the optical purity were measured for ethyl (S)-γ-bromo-β-hydroxybutyrate obtained by this reaction, in accordance with the same method as that in Example 1 described above. As a result, the yield in reaction was 84%, and the optical purity was 98% e.e.

Example 4

Ethyl (R)-5-amino-3-hydroxyvalerate was produced by using *Rosulomyces arthrosporioides* CBS 506.76 as the microbial cells and ethyl 5-amino-3-oxovalerate as the reaction substrate in accordance with the same procedure as that in Example 1. The yield in reaction and the optical purity were measured for ethyl (R)-5-amino-3-hydroxyvalerate obtained by this reaction, in accordance with the same method as that in Example 1 described above. As a result, the yield in reaction was 80%, and the optical purity was 92% e.e.

Example 5

Ethyl (R)-5-benzyloxycarbonylamino-3-hydroxyvalerate was produced by using *Rosulomyces arthrosporioides* CBS 506.76 as the microbial cells and ethyl 5-benzyloxycarbonylamino-3-oxovalerate as the reaction substrate in accordance with the same procedure as that in Example 1. The yield in reaction and the optical purity were measured for ethyl (R)-5-benzyloxycarbonylamino-3-hydroxyvalerate obtained by this reaction, in accordance with the same method as that in Example 1 described above. As a result, the yield in reaction was 66%, and the optical purity was 94% e.e.

Example 6

Ethyl (S)-γ-chloro-β-hydroxybutyrate was produced as follows by using *Aureobasidium pullulans* ATCC 34621, *Aureobasidium pullulans* MCI 3251 newly isolated by the present inventors from the nature, and *Aureobasidium pullulans* MCI 3252 newly isolated as well by the present inventors from the nature as described above.

Microbial cells of each of the microorganisms described above were respectively inoculated to a medium (each 100 ml) containing glucose (4.0 w/v %), yeast extract (2.0 w/v %), and corn steep liquor (0.5 w/v %) at pH adjusted to 6.0, and they were cultivated aerobically at 27° C. for 1 to 2 days with shaking. After completion of the cultivation, microbial cells were collected by centrifugation, and washed with phosphate buffer (0.1M, pH 6.5). After that, the respective microbial cells were suspended in the same buffer (100 ml) containing glucose (3.0 w/v %) so that the microbial cell concentration was the same as that in the culture broth. An aliquot (0.5 g) of ethyl γ-chloro-acetoacetate was added to each of the microbial cell suspensions to start a reaction with shaking at 27° C. Aliquots (each 0.5 g) of ethyl γ-chloro-acetoacetate were added six times at every 1 hour while maintaining pH at 6.5 with an aqueous solution of 1M Na$_2$CO$_3$ to perform the reaction with shaking for 7 hours in total.

After completion of the reaction, the produced amount and the optical purity were measured, and the absolute configuration was determined for ethyl (S)-γ-chloro-β-hydroxybutyrate obtained by the reaction by using each of the microbial strains, in accordance with the same method as that in Example 1 described above. Results are shown in Table 2.

TABLE 2

| Microorganism | Produced amount [g/L/broth] | Optical purity [% e.e.] | Absolute configuration |
|---|---|---|---|
| *Aureobasidium pullulans* ATCC 34621 | 20 | 99 | S |
| *Aureobasidium pullulans* MCI 3251 | 29 | 98 | S |
| *Aureobasidium pullulans* MCI 3252 | 32 | 99 | S |

According to the results described above, it is understood that the production method of the present invention makes it possible to produce the optically active ester of γ-substituted-β-hydroxybutyric acid having a high optical purity, in a short period of time at a high yield and a high accumulated concentration.

It is also understood that among the microorganisms used in Examples described above, when *Aureobasidium pullulans* is used for the method of the present invention, a reaction yield (in a larger production amount) and a optical purity of the produced optically active ester of γ-substituted-β-hydroxybutyric acid become higher.

It is further understood that the production method of the present invention is more effective when ethyl (S)-γ-chloro-β-hydroxybutyrate is produced from ethyl γ-chloro-acetoacetate.

What is claimed is:

1. A method for producing an optically active ester of γ-substituted-β-hydroxybutyric acid, comprising the steps of:

allowing microbial cells and/or a preparation therefrom of a microorganism to act on an ester of γ-substituted-acetoacetic acid represented by a general formula (1);

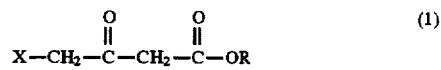

wherein X represents a halogen atom, a cyano group, or a protected or unprotected aminomethyl group, and R represents a lower alkyl group in the general formula (1);

wherein the microorganism has an ability to stereospecifically reduce a carbonyl group at a β-position of the ester of β-substituted-acetoacetic acid represented by the general formula (1), and the microorganism is selected from the group consisting of those belonging to the genera Yarrowia, Filobasidium, Metschnikowia, Galactomyces, Ambrosiozyma, Trichosporonoides, Aureobasidium, Phaeococcomyces, Rosulomyces, Dothichiza, Emericellopsis, Calonectria, Colletotrichum, and Ceratocystis; and stereospecifically reducing the carbonyl group at the β-position to produce the optically active ester of γ-substituted-β-hydroxybutyric acid represented by a general formula (2);

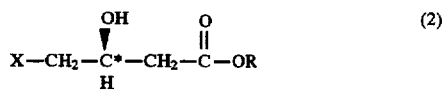

wherein X and R in the general formula (2) are synonymous with X and R in the general formula (1).

2. The method according to claim 1, wherein said microorganism is microorganism belonging to the genus Aureobasidium.

3. The method according to claim 2, wherein said microorganism is *Aureobasidium pullulans*.

4. The method according to claim 2, wherein said ester represented by the general formula (1) is ethyl γ-chloro-acetoacetate, and said ester represented by the general formula (2) is ethyl (S)-γ-chloro-β-hydroxybutyrate.

5. The method according to claim 3, wherein said ester represented by the general formula (1) is ethyl γ-chloro-acetoacetate, and said ester represented by the general formula (2) is ethyl (S)-γ-chloro-β-hydroxybutyrate.

6. The method according to claim 3, wherein said microorganism is *Aureobasidium pullulans*, a hyphal cell wall of which does not thicken.

7. The method according to any of claims 1 to 3 and 4, wherein said ester represented by the general formula (1) is ethyl γ-chloro-acetoacetate, and said ester represented by the general formula (2) is ethyl (S)-γ-chloro-β-hydroxybutyrate.

* * * * *